US006562834B2

(12) United States Patent
Bissery

(10) Patent No.: US 6,562,834 B2
(45) Date of Patent: May 13, 2003

(54) COMBINATION COMPRISING CAMPTOTHECIN AND A STILBENE DERIVATIVE FOR THE TREATMENT OF CANCER

(75) Inventor: Marie-Christine Bissery, Vitry sur Seine (FR)

(73) Assignee: Aventis Pharma S. A., Antony (FR)

( * ) Notice: Subject to any disclaimer, the term of this patent is extended or adjusted under 35 U.S.C. 154(b) by 0 days.

(21) Appl. No.: 09/984,043

(22) Filed: Oct. 26, 2001

(65) Prior Publication Data

US 2002/0115677 A1 Aug. 22, 2002

Related U.S. Application Data

(60) Provisional application No. 60/250,138, filed on Dec. 1, 2000, provisional application No. 60/245,582, filed on Nov. 6, 2000, and provisional application No. 60/243,341, filed on Oct. 25, 2000.

(51) Int. Cl.[7] ...................... A61K 31/05; A61K 31/135; A61K 31/436; A61K 31/437
(52) U.S. Cl. ........................ 514/283; 514/646; 514/734
(58) Field of Search ................. 514/283, 646, 514/734

(56) References Cited

U.S. PATENT DOCUMENTS

| 5,525,632 A | 6/1996 | Obsumi et al. ............. 514/646 |
| 5,674,906 A | 10/1997 | Hatanaka et al. ........... 514/626 |
| 6,104,894 A | 8/2000 | Sato et al. .................. 399/406 |

FOREIGN PATENT DOCUMENTS

| EP | 056692 | 7/1982 |
| EP | 074256 | 3/1983 |
| EP | 088642 | 9/1983 |
| EP | 137145 | 4/1985 |
| EP | 296612 | 12/1988 |
| EP | 321122 | 6/1989 |
| EP | 325247 | 7/1989 |
| EP | 540099 | 5/1993 |
| EP | 737686 | 10/1996 |
| JP | 57 116015 | 7/1982 |
| JP | 57 116074 | 7/1982 |
| JP | 59 5188 | 1/1984 |
| JP | 91 12070 | 3/1984 |
| JP | 60 19790 | 1/1985 |
| JP | 1 246287 | 10/1989 |
| JP | 1 249777 | 10/1989 |
| WO | WO 90/03169 | 4/1990 |
| WO | WO 96/37496 | 11/1996 |
| WO | WO 96/38146 | 12/1996 |
| WO | WO 96/38449 | 12/1996 |
| WO | WO 97/00876 | 1/1997 |
| WO | 00/33888 | * 6/2000 |
| WO | WO 02/056692 | 7/2002 |

OTHER PUBLICATIONS

Harrison's Principles of Internal Medicine, Eight Edition, 1977, pp. 1754–1755.*
P. Boyle, "Some Recent Developments in the Epidemiology of Colorectal Cancer," *Management of Colorectal Cancer*, Mosby, 1998, pp. 19–34.
Midgley R.S., et al., "Systemic Adjuvant Chemotherapy for Colorectal Cancer," *Managament of Colorectal Cancer*, Mosby, 1998, pp. 126–127.
T.H. Corbett et al., "Response of Transplantable Tumors of Mice to Anthracenedione Derivatives Alone and in Combination With Clinically Useful Agents," Cancer Treatment Reports, vol. 66, No. 5, 1982, pp. 1187–1200.
T.H. Corbett et al., "Evaluation of Single Agents and Combinations of Chemotherapeutic Agents in Mouse, Colon Carcinomas," Cancer, vol. 40, No. 5, 1977, pp. 2660–2680.
F.M. Schabel et al., "Testing Therapeutic Hypotheses In Mice and Man: Observations On the Therapeutic Activity Against Advanced Solid Tumors of Mice Treated With Anticancer Drugs That Have Demonstrated or Potential Clinical Utility For Treatment of Advanced Solid Tumors of Man," Cancer Drug Development, Part B. Methods in Cancer Research, vol. 17, New York, Academic Press Inc., 1979, pp. 3–51.
Emerson, D.L. et al., "In Vivo Antitumor Activity of To New Seven–substituted Water–soluble Camptothecin Analogues," Cancer Research, vol. 55, 1995, pp. 605–609.

* cited by examiner

Primary Examiner—Phyllis G. Spivack
(74) Attorney, Agent, or Firm—Finnegan, Henderson, Farabow, Garrett & DUnner LLP

(57) ABSTRACT

A pharmaceutical combination for the treatment of cancers containing a stilbene derivative and a camptothecin is described.

7 Claims, No Drawings

COMBINATION COMPRISING CAMPTOTHECIN AND A STILBENE DERIVATIVE FOR THE TREATMENT OF CANCER

This application relies on the benefit of priority of U.S. provisional patent application No. 60/243,341, filed Oct. 25, 2000; 60/245,582, filed Nov. 6, 2000; and 60/250,138, filed Dec. 1, 2000.

The present invention relates to therapeutic combinations comprising an effective amount of camptothecin (CPT-11) with an effective amount of a stilbene derivative, such as combretastatin, for the treatment for cancer.

The invention relates to the treatment of cancer, more especially solid tumors, most especially, non-small cell living cancer and colorectal cancer, with associations of camptothecin derivatives and other anticancer drugs and the use of such associations for an improved treatment.

More specifically, the invention relates to anticancer treatments with associations of irinotecan (CPT-11; Campto®) and a stilbene derivative, such as combretastatin.

Colorectal cancer is a leading cause of morbidity and mortality with about 300,000 new cases and 200,000 deaths in Europe and the USA each year (See P. Boyle, Some Recent Developments in the Epidemiology of Colorectal Cancer, pages 19–34 in *Management of Colorectal Cancer*, Bleiberg H., Rougier P., Wilke H. J., eds, (Martin Dunitz, London 1998); and—Midgley R. S., Kerr D. J., Systemic Adjuvant Chemotherapy for Colorectal Cancer, pages 126–27 in *Management of Colorectal Cancer*, Bleiberg H., Rougier P., Wilke H. J., eds, (Martin Dunitz, London 1998).)

Although about fifty percent of patients are cured by surgery alone, the other half will eventually die due to metastatic disease, which includes approximately 25% of patients who have evidence of metastases at time of diagnosis.

European patent EP 137,145, incorporated herein, describes camptothecin derivatives of the formula:

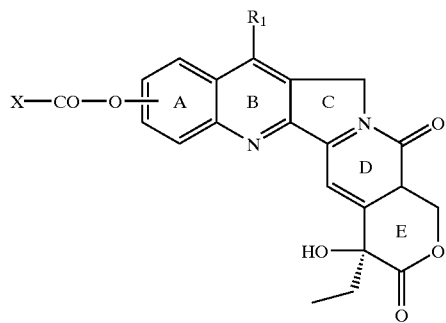

in which, in particular, $R_1$ is hydrogen, halogen or alkyl, X is a chlorine atom or $NR_2R_3$ in which $R_2$ and $R_3$, which may be identical or different, may represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S and/or $NR_4$, $R_4$ being a hydrogen atom or an alkyl radical and in which the group X—CO—O— is located in position 9, 10 or 11 on ring A.

These camptothecin derivatives are anticancer agents which inhibit topoisomerase I, among which irinotecan or CPT-11, in which X—CO—O— is [4-(1-piperidino-1-piperidino]carbonyloxy, is an active principle which is particularly effective in treatment of solid tumors, and in particular, colorectal cancer.

The European patent application EP 74,256 also describes other camptothecin derivatives which are also mentioned as anticancer agents, in particular, derivatives of a structure analogous to the structure given above and in which X—CO—O— is replaced with a radical —X'R' for which X' is O or S and R' is a hydrogen atom or an alkyl or acyl radical.

Other camptothecin derivatives have also been described, for example, in the patents or patent applications EP 56,692, EP 88,642, EP 296,612, EP 321,122, EP 325,247, EP 540,099, EP 737,686, WO 90/03169, WO 96/37496, WO 96/38146, WO 96/38449, WO 97/00876, U.S. Pat. No. 7,104,894, JP 57 116,015, JP 57 116,074, JP 59 005,188, JP 60 019,790, JP 01 249,777, JP 01 246,287 and JP 91 12070 or in Canc. Res., 38 (1997) Abst. 1526 or 95 (San Diego—April 12–16), Canc. Res., 55(3):603–609 (1995) or AFMC Int. Med. Chem. Symp. (1997) Abst. PB-55 (Seoul—July 27–August 1).

Camptothecin derivatives are usually administered by injection, more particularly intravenously in the form of a sterile solution or an emulsion. Camptothecin derivatives, however, can also be administered orally, in the form of solid or liquid compositions.

Camptothecin is a cytotoxic alkaloid which possesses strong anti-tumor activities. However, while camptothecin derivatives are considered as some of the most powerful substances possessing anti-tumor activity for colorectal cancer, the use of these compounds can be improved in clinical treatments by association with other antitumor agents.

It has now been found that the combination of a camptothecin derivative with a stilbene derivative is especially effective in the treatment of many solid tumors, including colorectal cancer. Among the effective stilbene derivatives is combretastatin A-4, and a derivative of that compound which will be called simply combretastatin. Both of these compounds exhibit strong mitosis inhibitory activities, cytotoxicity, and inhibit tubulin polymerization.

Combretastatin A-4 has the following formula:

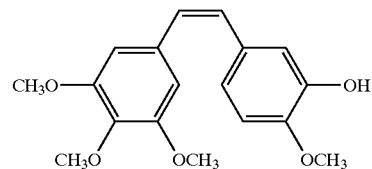

The combretastatin of this invention has the following formula:

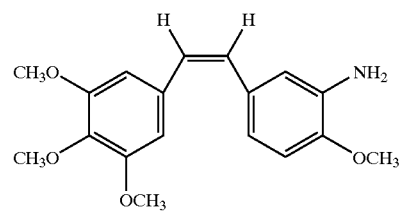

These combretastatins are soluble in water and can be used in the form of a salt exemplified by hydrochloride, acetate, phosphate, methanesulfonate, and the like.

The manufacture of stilbene derivatives, including combretastatin A-4, which may be in the form of pharmaceutically acceptable salts, hydrates and solvates, and the manufacture of oral and/or parenteral pharmaceutical composition containing the above compound, its inert pharmaceutically acceptable carrier(s) and/or diluent(s), are disclosed in U.S. Pat. No. 5,525,632. This patent and U.S. Pat. No. 5,674,906 disclose that stilbene derivatives, including combretastatin, when used alone, have low toxicity and carcinostatic effects in vivo.

It has recently been discovered that the combination of camptothecin and combretastatin significantly reduces the development of tumor volume over what would be predicted from administration to tumor-infected mammals of each compound alone. In fact, the sequential combination of CPT-11, a derivative of camptothecin, and the stilbene derivative, combretastatin, is more active at a lower dose than the highest non-toxic dose of each single agent for the treatment of cancers, especially in colon adenocarcinoma. See Table IV infra.

The efficacy of a combination may be demonstrated by determination of its therapeutic synergy. A combination manifests therapeutic synergy if it is therapeutically superior to one or other of the constituents used at its optimum dose (T. H. Corbett et al., Cancer Treatment Reports, 66, 1187 (1982)).

The efficacy of a combination may also be demonstrated by comparison of the maximum tolerated dose of the combination with the maximum tolerated dose of each of the separate constituents in the study in question. This efficacy may be quantified, for example by the $log_{10}$ cells killed, which is determined by the following formula:

$$log_{10} \text{ cells killed} = T-C(\text{days})/3.32 \times T_d$$

in which T–C represents the time taken for the cells to grow, which is the mean time in days for the tumors of the treated group (T) to reach a predetermined value (1 g for example) and the tumors of the control group (C) to reach the same value, and $T_d$ represents the time in days needed for the volume of the tumors in the control group to double. (T. H. Corbett et al., Cancer, 40, 2660.2680 (1977); F. M. Schabel et al., Cancer Drug Development, Part B, Methods in Cancer Research, 17, 3–51, New York, Academic Press Inc. (1979)). A product is considered to be active if $log_{10}$ cells killed is greater than or equal to 0.7. A product is considered to be very active if the $log_{10}$ cells killed is greater than 2.8.

In the present invention, a stilbene derivative, such as combretastatin, in an amount sufficient to inhibit tumor proliferation may be used with a camptothecin derivative, such as CPT-11, and administered to a mammal, in need of curing, alleviation, or prevention of tumors, especially a human being suffering from proliferation of tumor cells, in order to inhibit the growth of the tumor cells.

The inhibition of proliferation of tumor cells means inhibition of those tumor cells sensitive to therapy including administration of an effective amount of combretastatin and an effective amount of CPT-11 to a human being suffering from proliferation of tumor cells. In an acceptable case, this administration suppresses proliferation of tumor cells or diminishes the measurable size of the tumors. In an optimum case, the tumor undergoes regression completely.

As described above, there is no particular limitation to the method of administering the antitumor agents of the present invention to the mammal being treated. They may be administered orally or parenterally, such as by intravenous, subcutaneous or intramuscular route. For prompt efficacy, parenteral administration of combretastatin, such as by intravenous and subcutaneous administration, by infusion, etc. is preferred. In the method for administering the pharmaceutical preparation according to the present invention, combretastatin may be administered simultaneously with CPT-11 or the two may be sequentially administered in an optional order. In practice, the method and sequence for administration are varied depending on the individual preparation of combretastatin, the individual preparation of CPT-11, the individual tumor cells being cured, and the individual hosts being treated. The optimum method and sequence for administration of combretastatin and CPT-11 may be suitably selected by those skilled in the art with the aid of the routine technique and the information contained in the present specification.

An efficacious tumor proliferation inhibiting amount of the combretastatin and camptothecin means a curative unit inhibiting proliferation of the tumor cells sensitive to administration in the human being suffering from proliferation of tumor cells. The practically desirable curative unit is varied depending on the individual dosage forms of combretastatin used, the individual dosage forms of the CPT-11 used, the individual tumor cells being cured and the individual hosts being treated. The optimum curative units for preset given conditions may be suitably selected by those skilled in the art with the aid of the curative test units and the information contained in the present specification.

The antitumor agent of the present invention is a pharmaceutical preparation comprising at least the combretastatin and the camptothecin compound as described above, such that the two active ingredients may be contained as a mixture in a pharmaceutical preparation. However, the two active ingredients in the present invention may also be contained separately in distinct pharmaceutical preparations to be used sequentially and in combination. It is noted that such a pharmaceutical preparation containing other agents (third and fourth medical ingredients and so on) such as other antitumor agents, may naturally be encompassed by the present invention, insofar as the effective ingredients used in the present invention are contained in the pharmaceutical preparation. Moreover, it is possible for carriers, diluents and other substances, pharmaceutically acceptable for any of the pharmaceutical preparations in the present invention (a sole pharmaceutical preparation containing both ingredients in the present invention and separate pharmaceutical preparations separately each containing one of the two ingredients for use in combination) to be contained in the antitumor agent of the present invention.

Suitable pharmaceutically acceptable carriers and diluents, known to those skilled in the art of preparation of pharmaceutical preparations, may be used as appropriate in the antitumor agent(s) of the present invention. The antitumor agent of the present invention may be suitably applied parenterally, as discussed above. In this case, the antitumor agent(s) is prepared into an intravenous infusion or injection, along with pharmaceutically acceptable carriers by variable methods known to those skilled in the art. Preferably, the pharmaceutical agent is manufactured by a routine technique in, e.g., a unit dosage form and in the form of a freeze-dried mixture of two effective ingredients, and is re-prepared in water or other suitable liquid infusion in administration.

Twenty to 116.5 mg of combretastatin, preferably 36 to 60 mg., and 144 to 400 mg. of CPT-11, preferably 240 to 400 mg. of CPT-11, may be combined in each dosage of the pharmaceutical preparation according to the present invention. The physiological pharmaceutical value of the pharmaceutical composition used as an injection or infusion liquid is suitably adjusted by the content of a buffer well-known in the art.

The present invention is now explained in more detail with reference to preferred embodiments thereof. It is to be noted that these are given only as an examples and are not intended to limit the invention.

Antitumor Effect and Tests on Safety

The effect of the combination of CPT-11 and combretastatin was evaluated in mice bearing colon adenocarcinoma C51. CPT-11 was given orally on days two through five, four times daily, at different dosage levels. Combretastatin was administered intravenously, two times a day, on days one to five. In the combination arms, three different dosages of CPT-11 were administered orally twice daily on days two through five and three different dosages of combretastatin were administered intravenously twice a day on days one through five.

The results obtained in the study of single agents CPT-11 and combretastatin and the simultaneous combination CPT-11/combretastatin are given below in Table I.

TABLE I

Combretastatin (IV) in Combination with CPT-11 (oral)

| Combretastatin | CPT-11s | $Log_{10}$ Cell Kill | Colon 51 PR1 |
|---|---|---|---|
| Single Agents | | | |
| — | 400 | 1.1 | — |
| 116.5 | — | 1.3 | 5/5 |
| Simultaneous Combination | | | |
| 51.5 | 180 | 1.1 | 3/5 |

Tumor Size 400–500 mg; Td = 2.4 d
Schedule: CPT-11 4 x/day for 2–5 days; Combretastatin 2 x/day for 1–5 days
[1]Partial Response - Number of mice tested who have a decrease in tumor volume of at least 50%; i.e, of 5 mice tested, 5 had at least a partial response.

Table 1 illustrates the effects of combretastatin and CPT-11 as single agents given at their highest non-toxic doses. It also illustrates that when the anti-tumor compounds are given simultaneously, the cure rate is increased at reduced doses (45% of the highest non-toxic dose of the single agents). Thus, an effective treatment can be given at reduced toxicity.

Table II illustrates the sequential administration of combretastatin followed by CPT-11.

TABLE II

Sequential Combination of Combretastatin (IV) with CPT-11 (oral)

| Combretastatin | CPT-11 | $Log_{10}$ Cell Kill | Colon 51 PR |
|---|---|---|---|
| Combretastatin is Administered First | | | |
| 60 | 400 | Toxic | — |
| | 240 | 1.7 | 5/5 |
| | 144 | 1.5 | 5/5 |
| 36 | 400 | Toxic | — |
| | 240 | 1.4 | 5/5 |
| 21.6 | 400 | 1.4 | 4/5 |
| | 240 | 1.4 | 4/5 |

Combretastatin – HNTD = 116.5 mg/kg/injection – dose mg/kg/% of HNTD; 60 (51%); 36 (31%); 21.6 (18%). These doses alone do not induce regressions.

When combretastatin was administered first, the most efficient sequential combination was 60 mg/km of combretastatin (51% of HNTD), followed by 240 mg/kg of CPT-11(60% of HNTD). This combination resulted in a log cell kill of 1.7 and partial regression of the colon 51 tumor in all 5 mice tested. The combination was therefore therapeutically superior to both of the single agents used at their optimum dose.

While combretastatin, at 51% and 31% of its highest non-toxic dose, followed by the highest non-toxic dose of CPT-11 (400 mg/kg) was toxic to the test animals, only 18% of combretastatin in combination with the highest non-toxic dose of CPT-11 resulted in a $log_{10}$ cell kill of 1.4 and a partial response in all 5 of the tested. This log cell kill is higher than the log cell kill of each agent respectively and indicates the therapeutic efficacy of this combination.

Surprisingly, when 18% combretastatin was administered followed by CPT-11 at 60% of the highest non toxic dosage, the log cell kill remained the same (1.4) and showed marked efficacy.

Table III below shows that the sequential administration of CPT-11 first at its highest non toxic dose (400 mg/kg) followed by 36 mg/kg of combretastatin (31% of highest non-toxic dose) produced a $log_{10}$ cell kill of 1.9. Again, the $log_{10}$ cell kill of the highest non toxic dose of both CPT-11 and combretastatin as single agents was 1.1 and 1.3, respectively, indicating that this combination of CPT-11 followed by combretastatin possesses therapeutic synergy.

TABLE III

Sequential Combination with Combretastatin (IV) and CPT-11 (oral)

| CPT-11 is Administered First | | | |
|---|---|---|---|
| Combretastatin | CPT-11 | $Log_{10}$ Cell Kill | Colon 51 PR[2] |
| 60 | 400 | Toxic | |
| 36 | | 1.9 | 5/5 |
| 60 | 240 | Toxic | |
| 36 | | 1.4 | 5/5 |

Combretastatin, administered intravenously, and CPT-11, administered orally, were tested in several different schedules as reported in Table IV. When used as a single agent, combretastatin was administered twice a day for five consecutive days. When CPT-11 was administered alone, it was given once a day for four consecutive days.

When administered sequentially, two schedules were used. When combretastatin was given first, it was administered on day 1, followed by administration of CPT-11 once a day on days 2–5. When CPT-11 was the first compound given in the sequence, it was administered once a day on days 1–4, followed by combretastatin on day 5.

TABLE IV

Combination of Combretastatin (IV) with CPT-11 (oral) at Highest Non-Toxic Dose

| Combretastatin | CPT-11 | $Log_{10}$ Cell Kill | Colon 51 PR[2] |
|---|---|---|---|
| Single Agents | | | |
| — | 400 | 1.1 | — |
| 116.5 | — | 1.3 | 5/5 |
| Simultaneous Combination | | | |
| 51.5 | 180 | 1.1 | 3/5 |
| Sequential Combretastatin 1st | | | |
| 60.0 | 240 | 1.7 | 5/5 |
| Sequential CPT-11 1st | | | |
| 36.0 | 400 | 1.9 | 5/5 |

[2]Partial Response - No. of mice tested who have a decrease in tumor volume of at least 50%.

Table IV below shows that the sequential administration of combretastatin and CPT-11 in either order is substantially more effective than either of the compounds used alone or in simultaneous combination. It can be seen that the sequential combination of CPT-11/combretastatin is synergistically active against colon adenocarcinoma. Furthermore, the combination of CPT-11/combretastatin is more active at a lower dose than the highest non-toxic dose of either CPT-11 or combretastatin alone.

These tests show that combretastatin and CPT-11 may be administered in different ways so as to obtain the maximum efficacy of the compounds when used in combination. As a result, the invention is not limited to the compositions obtained by the physical association of the drugs, but also include those which permit separate administration, which can be simultaneous or sequential.

What is claimed is:

1. A synergistic pharmaceutical combination comprising camptothecin, or a derivative thereof and a stilbene derivative, wherein the stilbene derivative is a combretastatin chosen from:

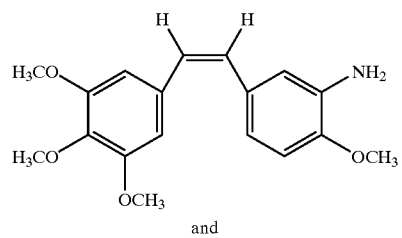

and

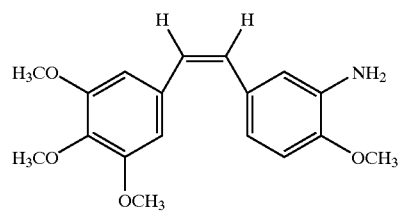

wherein said combination is synergistically therapeutic in solid tumors.

2. A synergistic pharmaceutical combination comprising an effective amount of CPT-11 and an effective amount of combretastatin for the treatment of solid tumors, wherein said combretastatin has the following formula:

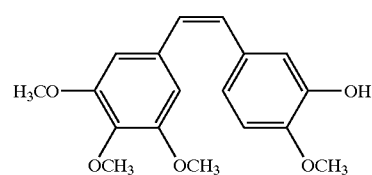

wherein said combination is synergistically therapeutic.

3. A method of treating solid tumors comprising administering sequentially an effective amount of CPT-11 followed by an effective amount of a combretastatin chosen from:

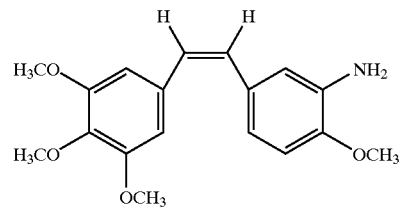

and

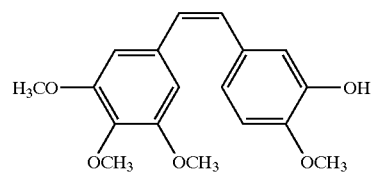

in order to produce a synergistic therapeutic effect.

4. The method according to claim 3, wherein said solid tumor is colon adenocarcinoma.

5. The method according to claim 3, wherein the dose of CPT-11 comprises from about 180 to about 400 mg/kg and the dose of combretastatin comprises about 36 mg/kg to 60 mg/kg.

6. The method according to claim 5, wherein the combination comprises a dosage level of 240 mg/kg of CPT-11 and 60 mg/kg of combretastatin.

7. A method of treating solid tumors comprising administering sequentially an effective amount of a combretastatin chosen from:

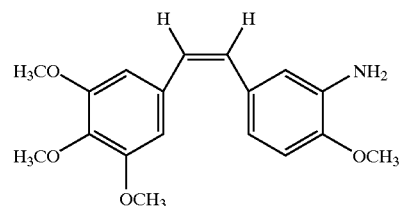

and

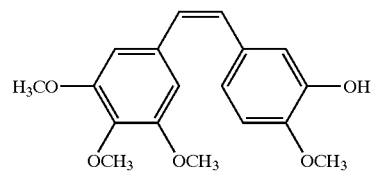

followed by an effective amount of CPT-11 in order to produce a synergistic therapeutic effect.

* * * * *